US00PP13466P3

(12) United States Plant Patent

Hoback, Jr.

(10) Patent No.: US PP13,466 P3
(45) Date of Patent: Jan. 7, 2003

(54) *VINCA MINOR* PLANT NAMED 'SUNNY SKIES'

(75) Inventor: Richard H. Hoback, Jr., Landenberg, PA (US)

(73) Assignee: CP Delaware, Inc., Wilmington, DE (US)

( * ) Notice: Subject to any disclaimer, the term of this patent is extended or adjusted under 35 U.S.C. 154(b) by 55 days.

(21) Appl. No.: 09/867,458

(22) Filed: May 31, 2001

(65) Prior Publication Data

US 2002/0184675 P1 Dec. 5, 2002

(51) Int. Cl.[7] ..... A01H 5/00
(52) U.S. Cl. ..... Plt./226

(58) Field of Search ..... Plt./226

*Primary Examiner*—Bruce R. Campell
*Assistant Examiner*—W C Haas
(74) *Attorney, Agent, or Firm*—Burns, Doane, Swecker & Mathis, LLP

(57) ABSTRACT

A new variety of *Vinca minor* is provided that is particularly well suited for growing as a distinctive ground cover. The new variety is a branch mutation of the 'Bowles' variety (non-patented in the United States) and unlike its parent displays attractive smooth irregularly variegated foliage of varying shades of golden yellow green and dark green. An upright mounding and trailing growth habit is exhibited. Attractive solitary bright violet-blue flowers are formed primarily during mid-spring. The available choices in ornamental ground covers are expanded.

1 Drawing Sheet

BACKGROUND OF THE INVENTION

The new *Vinca minor* variety of the present invention was discovered during September, 1996 at West Grove, Pa., U.S.A., as a branch sport of unknown causation of the 'Bowles' variety (non-patented in the United States). Such new variety has been carefully preserved and studied in view of its distinctive combination of characteristics. Had the new variety of the present invention not been discovered and preserved, it would have been lost to mankind.

It was found that the new *Vinca minor* variety of the present invention exhibits the following combination of characteristics:

(a) Forms attractive smooth irregularly variegated foliage of varying shades of golden yellow green and dark green,
(b) Displays an upright mounding and trailing growth habit,
(c) Forms attractive solitary bright violet-blue flowers, and
(d) Is particularly well suited for growing as a distinctive ornamental ground cover.

The new variety of the present invention can be readily distinguished from its 'Bowles' variety parent by the presence of the variegated foliage as described and illustrated. More specifically, the foliage of the 'Bowles' variety is totally lacking such variegation and possesses plain all-green leaves.

The new variety of the present invention well meets the needs of the horticultural industry and expands the choices of available ground covers. The bright violet-blue flowers appear during mid-spring and sporadically throughout the growing season.

Division and the rooting of cuttings have been used to asexually propagate the new variety at West Grove, Pa., U.S.A. It has been found that the distinctive combination of characteristics of the new variety is firmly fixed and is reliably transmitted to succeeding generations.

The new variety of the present invention has been named 'Sunny Skies'.

BRIEF DESCRIPTION OF THE PHOTOGRAPHS

The accompanying photographs show specimens of the new variety in color as nearly true as it is reasonably possible to make the same in color illustrations of this nature. The plants were approximately two years of age and were being grown in the landscape at West Grove, Pa., U.S.A.

DETAILED DESCRIPTION

Figure 1:
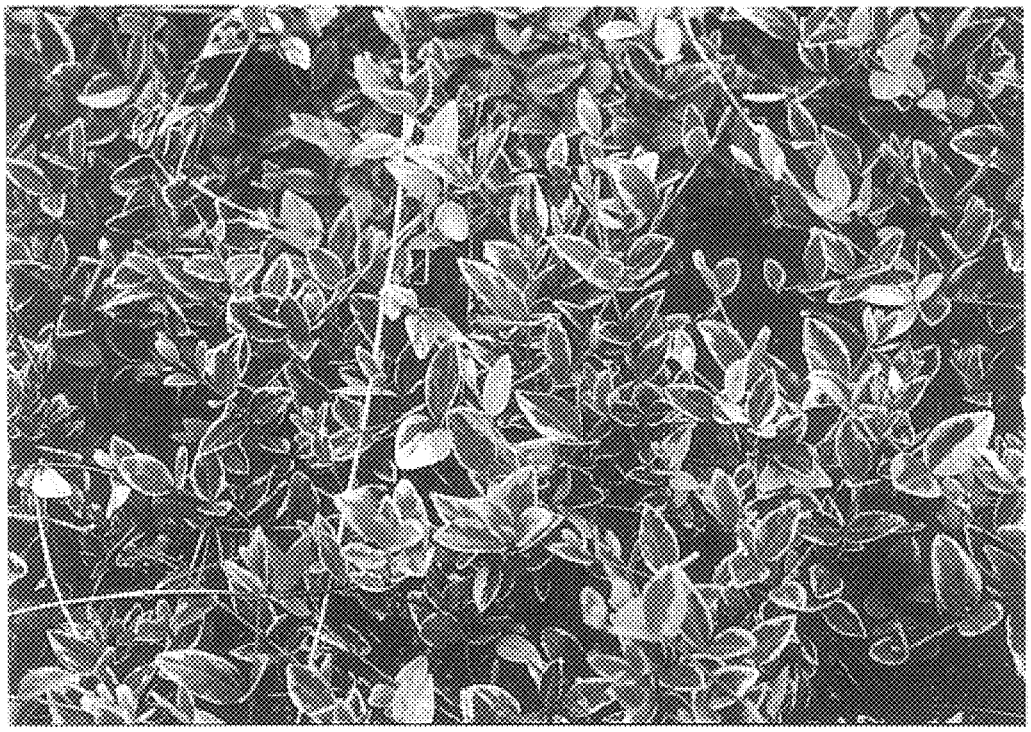
FIG. 1 illustrates the distinctive typical smooth irregularly variegated foliage of varying shades of golden yellow green and dark green of the new variety of the present invention.

The following is a detailed description of the new variety that was obtained while observing plants being grown outdoors at West Grove, Pa., U.S.A., during April. The plants were approximately two years of age and were being grown on their own roots under typical nursery growing conditions. The chart used in the identification of color is the R.H.S. Colour Chart of The Royal Horticultural Society, London, England. More common color terms are to be accorded their ordinary dictionary significance.

Botanical classification: *Vinca minor*, cv. 'Sunny Skies'.

Plant:

*Habit.*—Upright mounding and trailing with vertical growth being present from a central mounding mat.

*Height.*—Approximately 7.5 to 12.5 cm of annual growth.

*Width.*—Approximately 30 to 60 cm of annual growth.

Branches:

*Diameter.*—Approximately 1 to 2 mm.

*Length.*—Commonly vary from 30 to 120 cm.

*General appearance.*—Rounded and striated.

*Color.*—Young stems commonly are Yellow-Green Group 144C to 144D, and mature stems commonly are darker green, Yellow-Green Group 146B to 147C. The mature stems commonly display a slight pubescence having a coloration of near Greyed-White Group 156D.

*Internodes.*—Approximately 2 to 5 cm in length.

Leaves:

*Arrangement.*—Opposite.

*Length.*—For young leaves approximately 2.5 cm and for mature leaves approximately 4 cm.

*Width.*—For young leaves approximately 1.5 cm and for mature leaves approximately 2.5 cm.

*Shape.*—Ovate to elliptical. The apices are obtuse on young leaves and tend to be acute as the leaves mature. The bases are acute. The leaves are cupped with the margins being slightly higher than the midribs.

*Margins.*—Entire.

*Texture.*—Consistently smooth.

*General appearance.*—Smooth and semi-glossy.

*Color.*—Young Foliage: Commonly an irregular display on the dorsal surface of Yellow-Green Group 150B, Yellow-Green Group 151C to 151D, Green Group 141A to 141B, and Green Group 143C, and on the ventral surface of Greyed-Yellow Group 160B and Yellow-Green Group 151C to 154D. Mature Foliage: Commonly an irregular display on the dorsal surface of Yellow-Green Group 147A to 147B, Yellow-Green Group 147B to 147C, Yellow-Green Group 147C to 147D, and Yellow-Green Group 151B to 151C, and on the ventral surface of Yellow-Green Group 146B, Yellow-Green Group 147B, and Yellow-Green Group 151B to 151C.

*Midrib.*—The coloration is Yellow-Green Group 150C to 150D on the dorsal surface and Green Group 143C on the ventral surface.

*Petioles.*—The length is approximately 2 mm for young leaves and approximately 3 mm for mature leaves. The diameter is approximately 1 mm for both young leaves and mature leaves. The coloration is Green Group 143C on the dorsal surface and Green Group 143C to Green Group 143D on the ventral surface.

Inflorescence:

*Time of blossoming.*—Primarily during mid-spring and sporadically throughout the growing season.

*Calyx.*—Five in number, small, and possess linear lobes approximately 3 mm in length that are Yellow-Green Group 145C in coloration.

Figure 2:
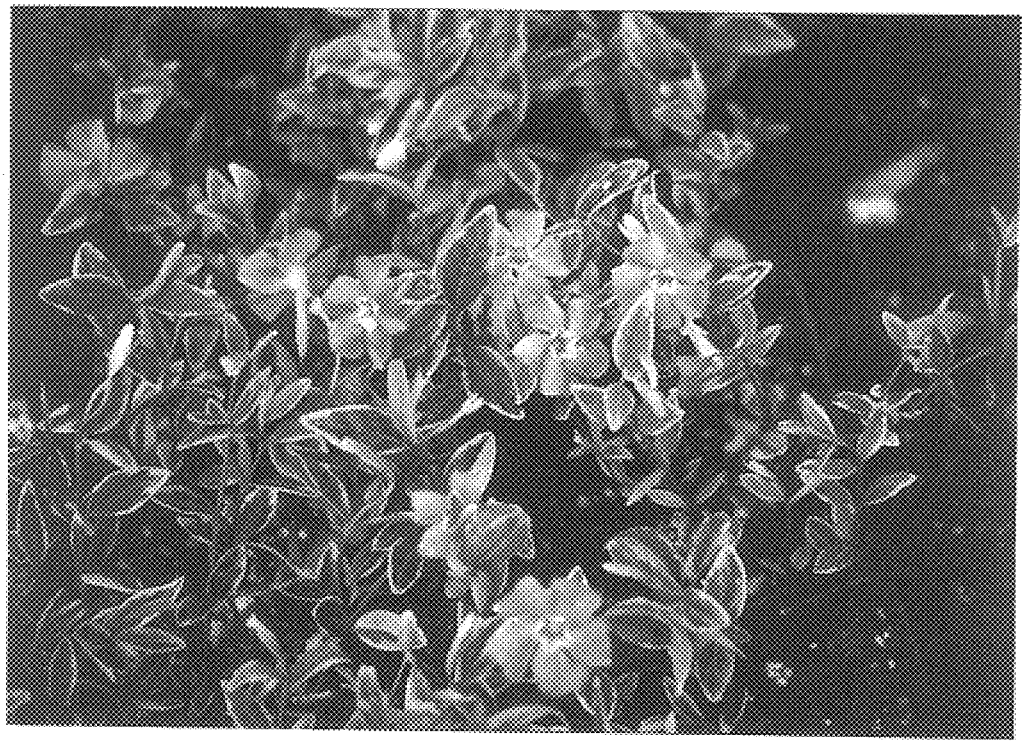
FIG. 2 illustrates a closer view of the typical solitary five-petaled bright violet-blue flowers of the new variety of the present invention as well as the distinctive variegated foliage.

*Corolla configuration.*—Perfect five-petaled flowers are borne from the leaf axis that initially are funnel-shaped prior to full opening as shown in FIG. 2.

*Bud size.*—Approximately 1.5 cm in length and approximately 4 mm in width.

*Corolla color.*—Before opening Violet-Blue Group 92A and 92B, and when opened Violet-Blue Group 92A and 92B on the dorsal surface and Violet-Blue Group 92B and 92C on the ventral surface.

*Reproductive parts.*—Five stamens and one pistil.

Development:

*Vegetation.*—Vigorous.

*Resistance to diseases.*—No particular susceptibility to diseases has been noted during observations to date.

I claim:

1. A new and distinct variety of *Vinca minor* plant that exhibits the following combination of characteristics:

(a) Forms attractive smooth irregularly variegated foliage of varying shades of golden yellow green and dark green,
(b) Exhibits an upright mounding and trailing growth habit,
(c) Forms attractive solitary bright violet-blue flowers, and
(d) Is particularly well suited for growing as a distinctive ornamental ground cover;

substantially as illustrated and described.

* * * * *